US007182599B2

(12) United States Patent
Stone et al.

(10) Patent No.: US 7,182,599 B2
(45) Date of Patent: Feb. 27, 2007

(54) METHOD AND APPARATUS FOR REMOVING PARTICULATE METALS FROM DENTAL WASTE WATER

(75) Inventors: Mark E. Stone, Wilmette, IL (US); Jeffrey M. Gullett, Louisville, KY (US); John C. Kuehne, Bisbee, AZ (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 34 days.

(21) Appl. No.: 11/152,340

(22) Filed: Jun. 15, 2005

(65) Prior Publication Data

US 2005/0282107 A1 Dec. 22, 2005

Related U.S. Application Data

(60) Provisional application No. 60/580,361, filed on Jun. 18, 2004.

(51) Int. Cl.
*A61C 17/06* (2006.01)
*B01D 21/00* (2006.01)

(52) U.S. Cl. .................. 433/92; 210/420; 210/424; 210/434

(58) Field of Classification Search .............. 433/92; 210/433.1, 434, 420, 424
See application file for complete search history.

(56) References Cited

U.S. PATENT DOCUMENTS

| | | | | |
|---|---|---|---|---|
| 188,274 A * | 3/1877 | Woolsey | | 210/317 |
| 1,237,577 A * | 8/1917 | Svendsen | | 210/420 |
| 3,746,033 A * | 7/1973 | Keiper, II | | 137/205 |
| 3,822,018 A * | 7/1974 | Krongos | | 210/323.2 |
| 3,853,761 A * | 12/1974 | McClory | | 210/100 |
| 3,907,688 A * | 9/1975 | Close | | 210/424 |
| 4,172,796 A * | 10/1979 | Corder | | 210/238 |
| 4,935,126 A * | 6/1990 | Drori | | 210/107 |
| 5,354,468 A * | 10/1994 | Richards | | 210/448 |
| 5,741,397 A * | 4/1998 | Kraver | | 159/25.2 |
| 6,149,812 A * | 11/2000 | Erickson | | 210/521 |
| 6,571,960 B2 * | 6/2003 | Williamson et al. | | 210/420 |
| 6,592,769 B1 * | 7/2003 | Erickson | | 210/801 |

* cited by examiner

*Primary Examiner*—Ralph A. Lewis
(74) *Attorney, Agent, or Firm*—Joseph K. Hemby, Jr.; Albert Churilla

(57) ABSTRACT

An inline filter assembly to be used in conjunction with surgical or other procedures, near the patient or chairside in dental operations, that is capable of removing, by filtration, particulate matter from waste-water. The filter assembly is configured to permit easy and rapid changing of filters. The filter assembly also contains a series of stopcocks to permit easy and quick changing of filters while maintaining suction to the patient.

7 Claims, 3 Drawing Sheets

METHOD AND APPARATUS FOR REMOVING PARTICULATE METALS FROM DENTAL WASTE WATER

CROSS-REFERENCE TO RELATED APPLICATION

This application claims priority to U.S. Provisional application 60/580,361 filed Jun. 18, 2004.

FIELD OF THE INVENTION

The inventive subject matter relates to the removal of particulate metals, such as mercury or silver from dental waste water using a self-contained mercury filtration cartridge for a single dental unit.

BACKGROUND OF THE INVENTION

Mercury removal systems are designed to remove only particulate waste (amalgam separators), or both particulate and dissolved waste from the dental waste-water slurry using a combination of gravity sedimentation, filtration, chemical oxidation, and ion-exchange materials.

Previously dental waste-water systems, such as those described in U.S. Pat. No. 3,138,873 to Bishop; U.S. Pat. No. 3,777,403 to Ritchie; U.S. Pat. No. 4,385,891 to Ligotti; U.S. Pat. No. 5,205,743 to Ludvigsson et al, were designed to remove dental waste, particularly amalgam. These systems make use of the suction stream to pass the slurry through filters. In these systems the mixture of liquid and solids pass and the solids settle and are removed by a combination of gravity sedimentation and filtration. The dental waste system disclosed in U.S. Pat. No. 5,795,159 to Ralls et al. is differentiated over previously disclosed systems by also incorporating different containers through which the mixture of liquid and solids pass, and solids settle and are removed utilizing the force of gravity and filtration. Most high efficiency waste-water removal systems are designed as centrally located systems, such as disclosed in U.S. Pat. No. 5,885,076 to Ralls, et al and U.S. Pat. No. 6,521,131 to Hamilton, et al. In addition to gravity sedimentation and filtration, these systems utilize a combination of chemical oxidation, precipitation, and/or ion-exchange materials through which the slurry is passed.

Centrally located systems suffer from a number of disadvantages including: 1) location of the apparatus at a distance from the source (i.e. the dental chair), which allows amalgam and mercury to settle and accumulate in dental office plumbing lines, eventually rendering these lines a hazardous waste material in themselves; 2) a requirement to accurately size the system relative to the number of dental chairs serviced, total waste-water accumulation and amount of amalgam waste produced per unit of time; 3) a relatively high level of complexity of installation; 4) an accumulation over time of amalgam waste sludge in settling tanks in addition to the collection within the filters; and 5) the complexity of chemical interactions that can occur over time, especially within holding tanks, between various materials, disinfectants, and chemicals used in the practice of dentistry (and contained within the waste-water slurry), and bacteria and waste materials that accumulate in settling tanks in constant contact with the waste-water slurry containing same. Interaction with various compounds in the holding tanks can result in significant environmental concerns due to chemical interactions or by bacterial conversion of inorganic elemental mercury to organic methyl mercury.

Therefore, despite the often efficient removal of dental waste by centrally located systems, the result can lead to the undertaking of costly hazardous material removal and storage procedures. The associated costs associated with handling and storage of relatively large volumes of material are often beyond the scope of ability of typical dental offices or even dental centers. These costs are further compounded by a the generation of multiple kinds of hazardous waste containers, each of which must be handled separately and using different means. These include: 1) particulate waste removed from the chair side amalgam trap, that are not part of the collection devices; 2) waste accumulated in dental office plumbing lines, which effectively become sedimentation collection lines, and which then represent a permanent residual source of mercury dissolution into the waste stream; 3) sedimentation (holding) tanks designed to collect settled particulate dental sludge; and 4) each of any number of various filters to remove successively finer particles and/or dissolved mercury from the dental waste-water effluent.

A filter apparatus disclosed in U.S. Pat. No. 5,630,939 to Bulard and Gillespie describes an in-line filter assembly capable of trapping tissue and other non-soluable matter during surgical operations. The device can be placed anywhere in the vacuum line. A feature of the apparatus is the ability to disconnect the line and remove the filter, along with trapped matter. However, in order for the filter to be replaced or cleaned, the vacuum must be broken and concomitantly service to the surgical patient. Therefore a need exists for a chairside filter device where filters can be replace on a routine basis without disruption of dental operations.

SUMMARY OF THE INVENTION

An object of the inventive subject matter relates to a self-contained mercury filtration cartridge for a single dental unit. This object is accomplished by passing dental waste through a self-contained apparatus containing a removable filter capable of removing non-soluable particles. The filter can be removed and replaced while maintaining vacuum to the patient and while still providing dental waste aspiration. An object of the invention, therefore, is an apparatus that permits filter cartridges to be easily replaced at regular intervals without disruption of vacuum and services to the patient. The cartridge can then be safely transported and stored, safely disposed of or recycled.

The inventive subject matter also relates to a self-contained mercury filtration device that removes all of the particulate dental waste material at a point closest to the source of the waste production, thereby preventing accumulation of waste in the plumbing lines and limiting interactions downstream in holding tanks.

DESCRIPTION OF THE PREFERRED EMBODIMENTS

Figure 1:
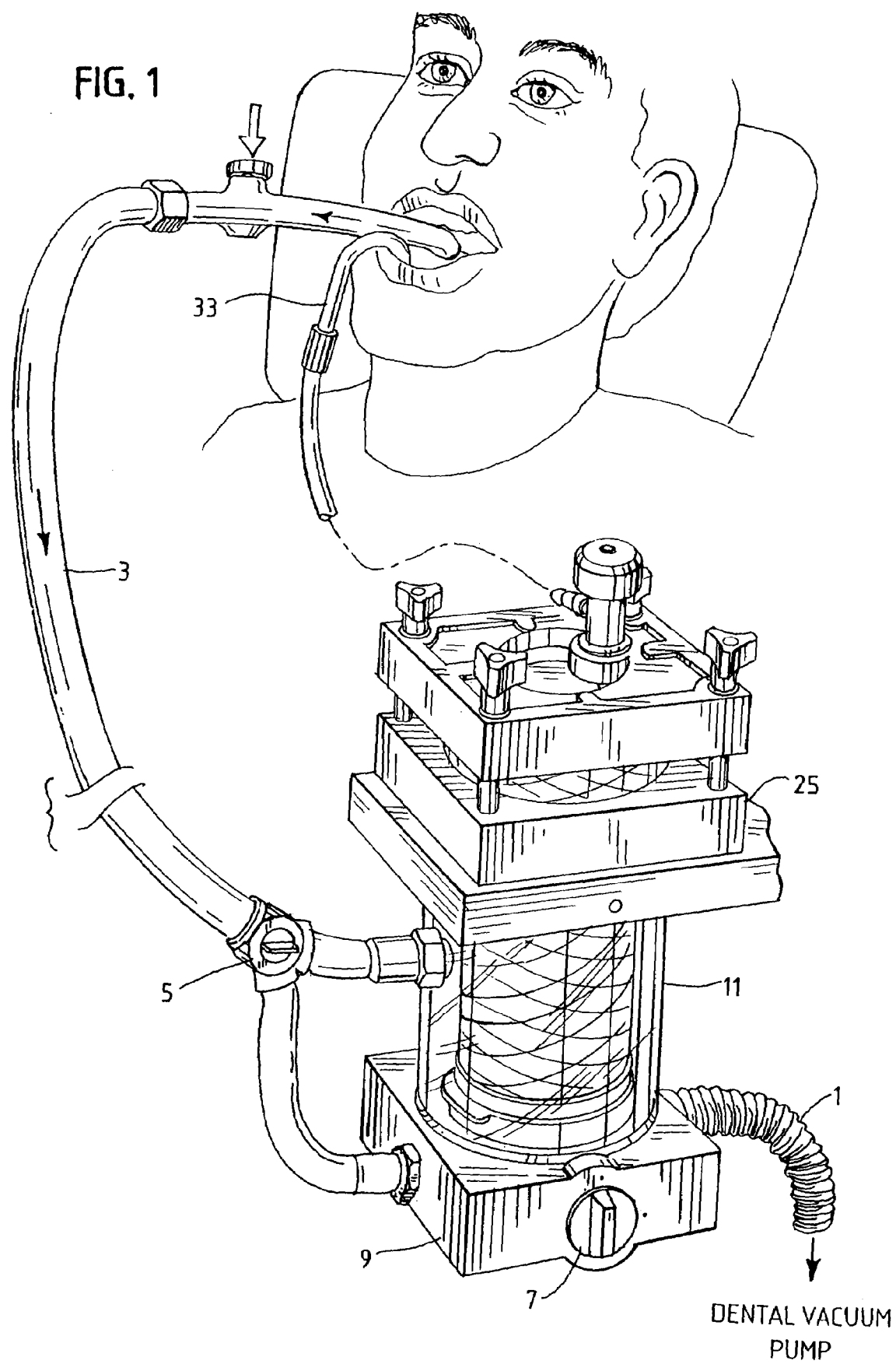
FIG. 1 is a view of the chairside, in-line placement of the apparatus.

Referring to FIG. 1, a preferred embodiment includes an apparatus placed at the dental chairside, in-line with a vacuum source 1 and the line from the dental patient 3. Dental waste-water can be collected in holding tanks and stored for later disposal. The apparatus contains a two-way inlet stop-cock 5 in-line with the line from the dental patient 3 and another two-way outlet stop-cock 7 in-line with the vacuum source 1. The size of apparatus may vary.

Figure 2:
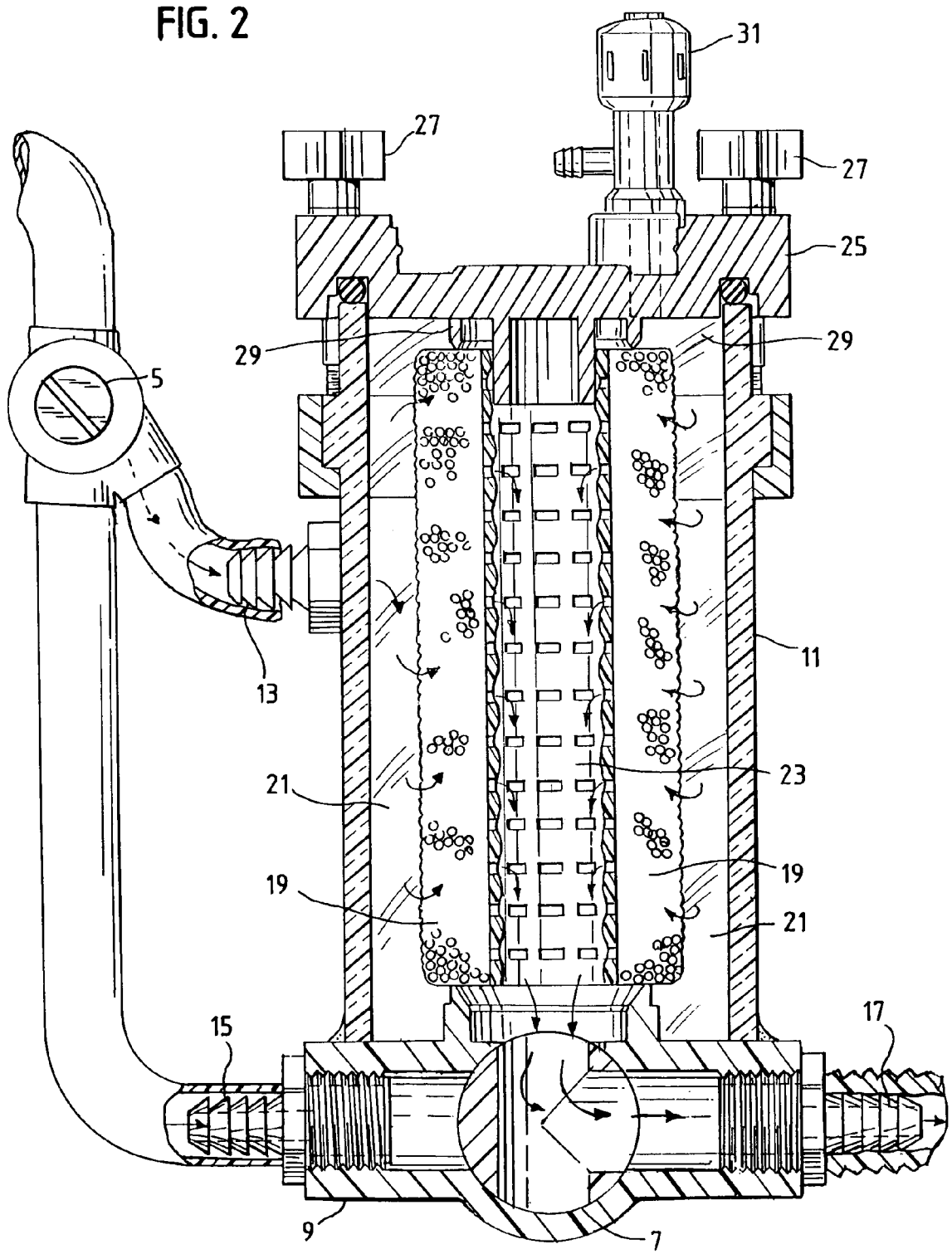
FIG. 2 is a cross-sectional view of the self-contained waste-water filtration cartridge.

Referring to FIG. 2, a cross-sectional view of the apparatus is shown. The apparatus contains a filter assembly 19 that fits inside the outer container 11 forming two spaces, an outer lumen 21 and a central lumen 23. The outer lumen is in direct communication with the filter waste-water inlet port 13. The outer and central lumen are separated by filter material of the filter assembly 19 and therefore are indirectly in communication. The filter waste-water inlet port 13 receives waste-water to be filtered via an inlet stop-cock 5. Water from the filter waste-water inlet port 13 flows into the outer lumen 21. The central lumen 23 is located over the inlet-side of an outlet stop-cock 7 that is in communication with the outlet port 17. The filter waste-water inlet port 13, outlet port 17 and filter assembly are positioned such that for waste-water to enter and exit the filter, fluid flow from the patient must pass into the outer lumen 21, through the filter and out, via the central lumen, through the outlet port. Therefore, referring to FIG. 2A, when the inlet stop-cock 5, supplying waste-water to be filtered, is opened in-line with the filter waste-water inlet port 13 and the outflow stop-cock 7 is opened in-line with the central lumen 23, dental waste-water flows into the outer lumen 21 of the outer container 11, through the filter 19 and into the central lumen 23 out through the outlet stop-cock 7 and out of the apparatus via the outlet port 17 and into the vacuum line 1. As the water passes through the filter particulate matter is trapped onto the filter. Waste-water, minus particulate matter, flows out through the outlet port and ultimately into the vacuum line 1. The inlet and outlet ports contain one-way check valves to prevent backflow of waste-water to the patient.

Referring to FIG. 2, opposite the apparatus base 9, is a gasket assembly 25 that is secured to the outer container. The gasket assembly 25 communicates with the outer container 11 and the filter assembly 19 such that it creates a vacuum seal to the central 23 and outer lumens 21 so that there is communication between the outer and central lumen only through the filter 19. The gasket assembly 25 is secured to the outer container by any number of means including screws or clamps 27. Vacuum seal is provided by the gasket assembly by any means including with the use of O-rings, rubber seals or seals made from other non-rubber materials 29. An additional inlet port 31 is also located on the gasket assembly 25 that provides suction, at a reduced vacuum compared to the patient line 3, to the outer lumen.

Figure 2A:
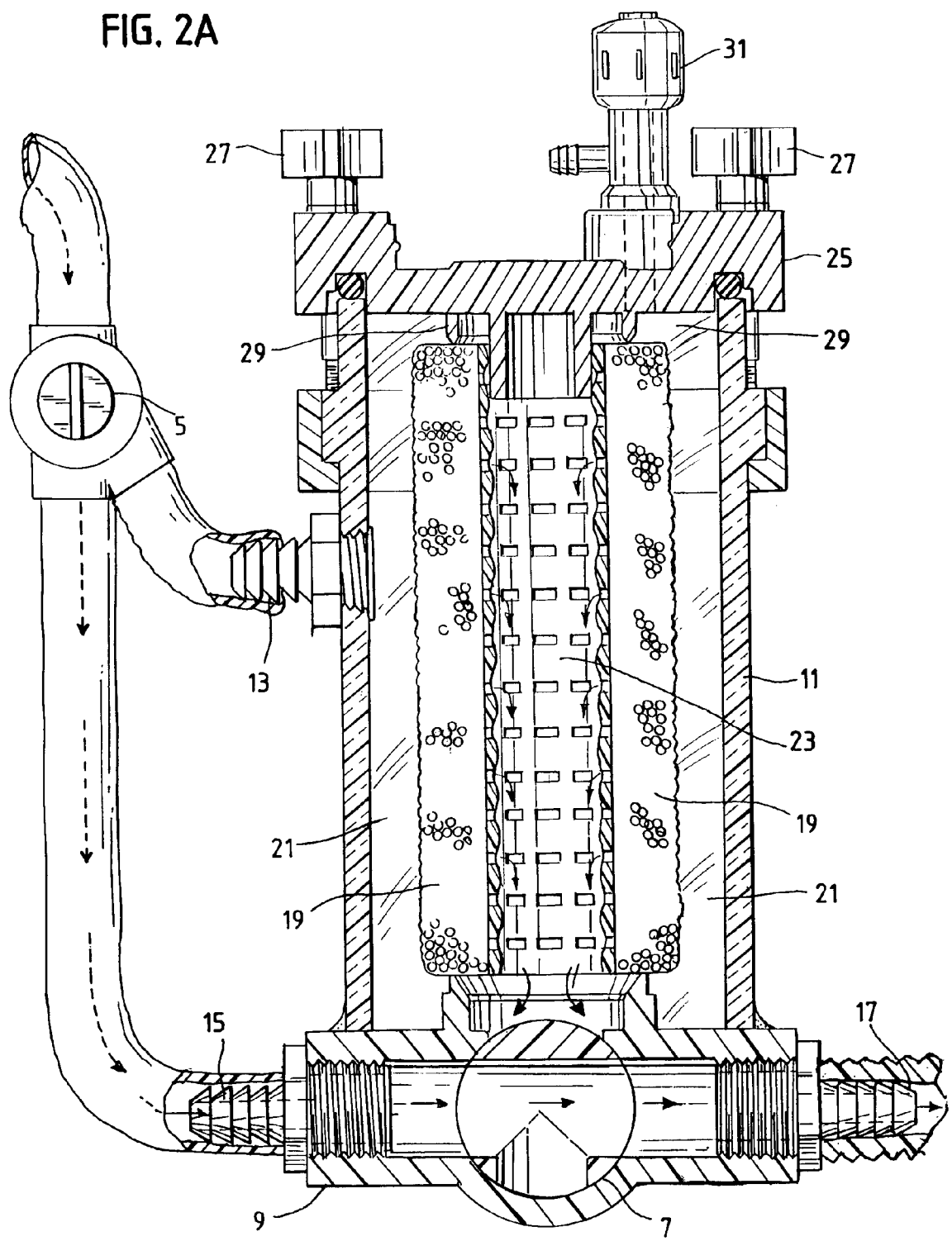

Referring to FIG. 2A, the apparatus can also be operated such that the stop-cock value assembly will permit direct, in-line communication between the line from the patient 3 and the vacuum line 1. This is accomplished by adjusting the inlet flow stop-cock 5 and outlet stop-cock 7 such that they are both in-line with the nonfilter waste-water inlet port 15 on outer container base 9. In this configuration, the flow of dental waste-water is from the patient and directly into the vacuum line 1. Like the filter waste-water inlet port and outlet port, the nonfilter water-waste inlet contains a one-way check valve to prevent backflow. In this configuration the filter can be changed without disruption of vacuum service to the patient or dental operations by opening the gasket assembly and inserting a new filter assembly without disruption of vacuum to the patient or dental operations. After replacement of a new filter, the stop-cocks can be re-adjusted to return flow back through the filter assembly 19.

The outer container can be manufactured from any material including metal or plastic. A preferred embodiment is to manufacture the outer container out of clear plastic to permit constant evaluation of fluid container contents. Furthermore, the size of the apparatus can vary considerably depending on the number of chairs being serviced by the apparatus. Also, the shape of the apparatus can also vary widely. A preferred embodiment is for the shape of the device to be cylindrical. However, the height of the apparatus can be varied along with the cylindrical diameter.

The filter may be may be made of a variety of appropriate synthetic or natural materials, either spun or chemically manufactured, and may vary in pore size, depending on individual needs and availability. A preferred embodiment is for the filter pore size to be from 0.2 µm to 10 µm. Because flow can be interrupted without disruption of vacuum to the patient, filters can be changed mid-dental operation.

Obviously, many modifications and variations of the present invention are possible. It is therefore to be understood that, within the scope of the appended claims, the invention may be practiced otherwise than as specifically described.

We claim:

1. A self-contained waste-water filtration apparatus comprising:
   a. an outer cylindrical container having an inside portion and an upper, bottom and a base portion;
   b. a filter assembly, having a top and bottom portion, disposed lengthwise in the center of said inside portion of said outer container, having an inner side and an outer side, said inner side facing said center and defining an open central lumen area extending lengthwise in the center of said inside portion, the circumference of said outer side defining an outer lumen extending the length of and to the inside portion of said outer container with the bottom portion of said filter being secured by said base portion of said outer container;
   c. an inlet stopcock that is adapted to be in direct communication with a line from a patient, a filter waste-water inlet line and a nonfilter waste-water line, where said filter waste-water inlet line extends from said inlet stopcock through said outer container via a filter waste-water inlet port and into said outer lumen and where said nonfilter waste-water line extends from the stop-cock to a nonfilter waste-water inlet port where said nonfilter waste-water inlet port extends trough said base portion of said outer container but does not extend through said bottom portion of said outer container;
   d. an outlet port extending into said base portion and in communication with an outlet stop-cock where said outlet stop-cock is disposed between and in communication with said nonfilter waste-water inlet and outlet ports to allow flow either from said nonfilter waste-water inlet port directly to said outlet port or flow from said central lumen to said outlet port;
   e. a gasket assembly, said gasket assembly being disposed on said upper portion of said outer container and said top portion of said filter for securing said filter and providing a fluid and vacuum tight seal between outer lumen and central lumen.

2. The waste-water filtration apparatus of claim 1, wherein said gasket assembly contains a low vacuum inlet extending through said gasket assembly and into said outer lumen.

3. The waste-water filtration apparatus of claim 1, wherein said filter assembly removes metal containing particulate materials from dental waste-water.

4. The waste-water filtration apparatus of claim 3, wherein said metal comprises mercury or silver.

5. The waste-water filtration apparatus of claim 1, wherein said inlet and outlet ports contain a one-way check valve.

6. The waste-water filtration apparatus of claim 1, wherein said filter is manufactured from plastic, semi-rigid materials selected from the group consisting of polyvinyl chloride, fiberglass, rubber, polyethylene, and polypropylene.

7. The waste-water filtration apparatus of claim 1, wherein said filter has a pore size of 0.2 μm to 10 μm.

* * * * *